United States Patent
Zong

(10) Patent No.: US 8,501,717 B2
(45) Date of Patent: Aug. 6, 2013

(54) METHODS TO TREAT AND/OR PREVENT MUCOSITIS

(75) Inventor: Chen Zong, Metuchen, NJ (US)

(73) Assignee: Merck, Sharp & Dohme Corp., Rahway, NJ (US)

( * ) Notice: Subject to any disclaimer, the term of this patent is extended or adjusted under 35 U.S.C. 154(b) by 672 days.

(21) Appl. No.: 12/524,683

(22) PCT Filed: Feb. 8, 2008

(86) PCT No.: PCT/US2008/001716
§ 371 (c)(1),
(2), (4) Date: May 6, 2010

(87) PCT Pub. No.: WO2008/097646
PCT Pub. Date: Aug. 14, 2008

(65) Prior Publication Data
US 2010/0227005 A1    Sep. 9, 2010

Related U.S. Application Data

(60) Provisional application No. 60/889,097, filed on Feb. 9, 2007.

(51) Int. Cl.
| A61K 33/08 | (2006.01) |
| A61K 31/59 | (2006.01) |
| A61K 38/40 | (2006.01) |
| A61K 38/00 | (2006.01) |
| A61P 35/00 | (2006.01) |
| A61P 31/00 | (2006.01) |
| A61P 29/00 | (2006.01) |

(52) U.S. Cl.
USPC .................. 514/167; 514/12; 514/2; 424/684

(58) Field of Classification Search
USPC ...................... 514/167, 168, 12, 2; 424/684
See application file for complete search history.

(56) References Cited

U.S. PATENT DOCUMENTS

| 6,503,893 | B2 | 1/2003 | Bishop et al. |
| 6,566,353 | B2 | 5/2003 | Bishop et al. |
| 6,573,256 | B2 | 6/2003 | Bishop et al. |
| 2004/0009958 | A1 | 1/2004 | Bishop et al. |
| 2007/0238755 | A1 * | 10/2007 | Hauer-Jensen et al. ....... 514/337 |

FOREIGN PATENT DOCUMENTS

| WO | WO01/22907 | 4/2001 |
| WO | WO03/024391 | 3/2003 |
| WO | WO2004/043360 | 5/2004 |
| WO | WO2004/110151 | 12/2004 |
| WO | WO2004/110380 | 12/2004 |
| WO | WO2005/016872 | 2/2005 |
| WO | WO2006/116204 | 11/2006 |
| WO | WO2007/038428 | 4/2007 |
| WO | WO 2007/038428 | * 4/2007 |

OTHER PUBLICATIONS

International search report, PCT/US2008/001716 (Apr. 6, 2008).
International Preliminary Report on Patentability, PCT/US2008/001716 (Apr. 11, 2009).
Written Opinion of the International Searching Authority, PCT/US2008/001716 (2009).
Srinivas S, Feldman D., A phase II trial of calcitriol and naproxen in recurrent prostate cancer. Anticancer Res. Sep. 2009;29(9):3605-10.
Beer TM. Ascent: the androgen-independent prostate cancer study of calcitriol enhancing taxotere.BJU Int. Sep. 2005;96(4):508-13.
Tiffany NM, Ryan CW, Garzotto M, Wersinger EM, Beer TM. High dose pulse calcitriol, docetaxel and estramustine for androgen independent prostate cancer: a phase I/II study.J Urol. Sep. 2005;174(3):888-92.
Beer TM, Myrthue A, Garzotto M, O'hara MF, Chin R, Lowe BA, Montalto MA, Corless CL, Henner WD. Randomized study of high-dose pulse calcitriol or placebo prior to radical prostatectomy. Cancer Epidemiol Biomarkers Prev. Dec. 2004;13(12):2225-32.
Squier CA, Kremer MJ. Biology of oral mucosa and esophagus. J Natl Cancer Inst Monogr. 2001;(29):7-15. Review.

* cited by examiner

*Primary Examiner* — San-Ming Hui
*Assistant Examiner* — Kathrien Cruz

(57) ABSTRACT

The present invention relates to methods useful for treating and/or preventing mucositis using an active vitamin D compound.

33 Claims, No Drawings

METHODS TO TREAT AND/OR PREVENT MUCOSITIS

The present invention claims the benefit of U.S. provisional application no. 60/889,097, filed Feb. 9, 2007; which is herein incorporated by reference in its entirety.

FIELD OF THE INVENTION

The present invention relates to the use of active vitamin D compounds (including derivatives, homologs and mimics thereof) to treat and/or prevent mucositis.

BACKGROUND OF THE INVENTION

Mucositis is defined as inflammation and ulceration of the mucous membranes, and is a common dose-limiting toxic reaction to chemotherapy and radiotherapy. The affected mucous membrane may be in oral tissues, lung tissues, intestines or other organs. For a general background on mucositis, see Sonis et al., *Cancer Suppl.*, vol. 100, no. 9, pp. 1995-2025 (2004).

Among other radiation- and/or chemical-induced toxicity in non-malignant tissues, mucositis is a common and potentially serious side effect. In fact, oral mucositis has been identified as the most debilitating side effect of anticancer therapy by patients who experienced it while undergoing myelotoxic therapy for hematopoietic stem cell transplantation. Patients suffering from severe oral mucositis may find daily activities such as eating, drinking, swallowing, and talking difficult or impossible. When treated to ameliorate and/or prevent radiation- and/or chemical-induced toxicity in non-malignant tissues, patients receiving therapeutic radiation and/or chemical treatments may experience a higher quality of life and thereby remain on their therapeutic regimen so that the therapeutic effect may be achieved or possibly receive a more demanding and more effective therapeutic regimen.

In mucositis, the degree of injury to mucosal tissue is directly related to the type, dose, or dose intensity of the radiotherapy and/or chemotherapy regimens employed. Non-limiting examples of drugs that can result in mucositis include: anthracyclines (such as daunorubicin, doxorubicin, pirubicin, idarubicin and mitoxantrone), methotrexate, dactinomycin, bleomycin, vinblastine, cytarabin, fluorouracil, mitramycine, taxanes (such as docetaxel and paclitaxel), ifosfamide/eoposide, irinotecan, platinum, as well as combinations including one or more of these drugs.

Non-therapeutic radiation and/or chemical exposure, as may happen from accidents, acts of war, acts of civilian terrorism, space flights, or rescue and clean-up operations can also result in mucositis. In these scenarios the effects of radiation in the hematopoietic system and the gastrointestinal tract are critical.

Several agents have been investigated in order to find optimal management principles for mucositis and even though some agents have shown some prophylactic effect, no agent has been shown to be efficient in all settings. Thus, a need exists for methods of treating and/or preventing mucositis regardless of its cause.

Vitamin D is a fat-soluble vitamin essential as a positive regulator of calcium homeostasis. The hormonally active form of vitamin D is $1\alpha,25$-dihydroxyvitamin D3, also known as calcitriol. Calcitriol is a steroid hormone synthesized from dietary precursors. Dietary 7-dehydrocholesterol is converted to vitamin D3 by ultraviolet light absorbed through the skin. Vitamin D3 is hydroxylated at the 25 position by the liver and at the 1 position by the kidneys, converting it to the biologically active form, calcitriol. $1\alpha$-hydroxyvitamin D3, also known as 1a-calcidol, and 25-hydroxyvitamin D3, also known as calcifediol, are monohydroxylated vitamin D3 and may be converted to calcitriol upon hydroxylation by the liver and kidney, respectively. Specific nuclear receptors for active vitamin D compounds have been discovered in cells from diverse organs not involved in calcium homeostasis. Thus, in addition to influencing calcium homeostasis, active vitamin D compounds have been implicated in variety of biological processes.

In connection with the treatment of hyperproliferative diseases, it has been shown that the problem of systemic hypercalcemia can be overcome by "high dose pulse administration" (HDPA) of a sufficient dose of an active vitamin D compound to give an antiproliferative effect while avoiding the development of severe symptomatic hypercalcemia. According to U.S. Pat. No. 6,521,608, the active vitamin D compound may be administered no more than every three days, for example, once a week at a dose of at least 0.12 μg/kg per day (8.4 μg in a 70 kg person). Pharmaceutical compositions used in the HDPA regimen of U.S. Pat. No. 6,521,608 comprise 5-100 μg of active vitamin D compound and may be administered in the form for oral, intravenous, intramuscular, topical, transdermal, sublingual, intranasal, intratumoral, or other preparations.

SUMMARY OF THE INVENTION

The invention relates to methods for treating or preventing mucositis comprising the use of an active vitamin D compound.

In one embodiment, the invention relates to a method for treating and/or preventing mucositis in a subject in need thereof comprising administering to the subject a therapeutically effective amount of an active vitamin D compound. The active vitamin D compound could be any active vitamin D compound, analog, derivative or mimic thereof. In one embodiment, the active vitamin D compound is selected from the group consisting of calcitriol, $1\alpha$-cacidol and calcifediol. In another embodiment, the active vitamin D compound is calcitriol.

In one embodiment, the active vitamin D compound is administered by high pulse dose administration (HPDA). In one embodiment, the active vitamin D compound is administered by HPDA at a sufficient dose to provide a therapeutic effect without inducing severe symptomatic hypercalcemia. In certain preferred embodiments, the HDPA is administered no more frequently than once in three days.

In certain embodiments, the active vitamin D compound is administered in an amount sufficient to reach supraphysiologic levels (for example levels greater than about 0.25 nM, and more preferably at or above 1 nM) without inducing severe symptomatic hypercalcemia. In one embodiment, the active vitamin D compound is administered in an amount sufficient to reach blood plasma levels greater than about 0.25 nM. In another embodiment, the active vitamin D compound is administered in an amount sufficient to reach blood plasma levels equal to or greater than 1 nM.

In one embodiment, the active vitamin D compound is administered in an amount sufficient to reach supraphysiologic levels (for example levels greater than about 0.25 nM, and more preferably at or above 1 nM) within a period of time of about 2 hours after administration to about 36 hours after administration (preferably within 24 hours after administration) without inducing severe symptomatic hypercalcemia. In one embodiment, the active vitamin D compound is administered in an amount sufficient to reach blood plasma levels equal to or greater than 1 nM within 2 to 36 hours after administration. In another embodiment, the active vitamin D compound is administered in an amount sufficient to reach blood plasma levels equal to or greater than 1 nM within 2 to 24 hours after administration.

In one embodiment, the active vitamin D compound is administered in an amount sufficient to reach supraphysiologic levels (for example levels greater than about 0.25 nM, and more preferably at or above 1 nM) within a period of time of about 2 hours after administration to about 36 hours after administration (preferably within 24 hours after administration), and resulting in normal physiological levels (for example, levels at or below 0.16 nM) within 48 to 72 hours of administration.

In one embodiment, the active vitamin D compound is administered in an amount sufficient to maintain the patient's plasma level of the active vitamin D compound at or above 1 nM for 24 hours.

In one embodiment, the active vitamin D compound is administered in an amount sufficient to achieve an area under the curve "AUC" concentration of equal to or greater than 24 nM·hour. In another embodiment, the active vitamin D compound is administered in an amount sufficient to achieve an area under the curve "AUC" concentration of equal to or greater than 24 nM·hour, with the plasma concentration returning to normal physiological levels by 48-72 hours.

In one embodiment, the mucositis to be treated or prevented is oral mucositis. In another embodiment, the mucositis to be treated or prevented is gastrointestinal mucositis.

In other embodiments, the subject to be treated is suffering from mucositis or is at risk of developing mucositis. In certain embodiments, the subject has received or will be receiving radiation therapy or chemotherapy. In certain embodiments, the mucositis is caused or is likely to result from radiation-induced toxicity in non-malignant tissue. In other embodiments, the mucositis is caused or is likely to result from chemical-induced toxicity in non-malignant tissue. In one embodiment, the chemical-induced toxicity is not caused by docetaxel.

In one embodiment, the subject to be treated is a bone marrow patient. In another embodiment, the subject to be treated is a cancer patient. The subject may have any type of cancer. In certain embodiments, the subject has leukemia, lymphoma, rectal or colorectal cancer, breast cancer, prostate cancer, androgen-dependent prostate cancer, lung cancer, mesothelioma, head and neck cancer, esophageal cancer, gastric cancer, pancreatic cancer, gastrointestinal cancer, renal cell cancer, testicular cancer, germ cell cancer, glioma or any other primary or solid tumor. In one embodiment, the subject does not have androgen-independent prostate cancer.

The active vitamin D compound can be administered at any therapeutically effective amount. In one embodiment, the active vitamin D compound is administered at a dose of about 3 µg to about 1 mg. In one embodiment, the active vitamin D compound is administered at a dose of about 15 µg to about 1 mg. In another embodiment, the active vitamin D compound is administered at a dose of about 15 µg to 60 µg. In another embodiment, the active vitamin D compound is administered at a dose of about 30 µg to 60 µg. In another embodiment, the active vitamin D compound is administered at a dose of about 45 µg.

In certain embodiments, the active vitamin D compound is administered as a unit dosage form comprising about 10 µg to about 75 µg of calcitriol, about 50% MIGLYOL 812™ and about 50% tocopherol peg-1000 succinate (vitamin E TPGS). In one preferred embodiment, the active vitamin D compound is administered as a unit dosage form comprising about 45 µg of calcitriol, about 50% MIGLYOL 812 and about 50% tocopherol peg-1000 succinate (vitamin E TPGS).

The active vitamin D compound can be administered by any route. In one embodiment, the active vitamin D compound is administered orally, intravenously, parenterally, rectally, sublingually, intramuscularly, topically, nasally or transdermally. In a preferred embodiment, the active vitamin D compound is administered orally. In another preferred embodiment, the active vitamin D compound is administered intravenously.

The active vitamin D compound can be administered alone or with any other therapeutic agent(s) and/or modality(ies). In one embodiment, the active vitamin D compound is administered in combination with radiation therapy. In another embodiment, the active vitamin D compound is administered in combination with a chemotherapeutic agent. In another embodiment, the active vitamin D compound is administered with another agent used to treat mucositis. Agents that could be used to treat mucositis are known in the art. In one embodiment, the active vitamin D compound is administered in combination with an anti-fungal, an anti-bacterial, an anti-viral, an anesthetic or a gastrointestinal agent. In one embodiment, the active vitamin D compound is administered with a mouthwash or an oral care product. In one embodiment, the active vitamin D compound is administered with an immunomodulatory agent. In one embodiment, the active vitamin D compound is administered in combination with a protease activated receptor-1 (PAR-1) inhibitor. In another embodiment, the active vitamin D compound is administered in combination with an agent selected from the group consisting of: keratinocyte growth factor, GM-CSF (molgramostin), transforming growth factor 3, amifostin, a PAR-1 inhibitor, Kepivance™ (palifermin), glutamine, L-glutamine, teduglutide, sucralfate mouth rinses, iseganan, lactoferrin, mesna, trefoil factor, CASAD (a calcium alumino-silicate anti-diarrheal from NewCo Pharmaceuticals LLC) or a combination of two or more of the above. In another embodiment, the active vitamin D compound is administered in combination with another radiation-response modifier.

DETAILED DESCRIPTION OF THE INVENTION

The invention relates to the use of active vitamin D compounds (including homologs, derivatives and mimics thereof) to treat or prevent mucositis.

As used herein, "mucositis" refers to pain, redness, inflammation, ulceration, or combinations thereof, affecting the gastrointestinal tract from the mouth to anus, which results from disease or is secondary to therapeutic treatments such as certain chemotherapies, radiation, or combinations thereof, or is secondary to any mucositis-inducing circumstance or event.

Mucositis progresses in five phases as detailed below. Phase 1, "the initial phase," includes: DNA strand breaks, and reactive oxygen species generation. Phase 2, "the primary damage response phase" includes: activation of NF-kB and p53 pathway; NF-κB up-regulation of genes that may exert an effect on mucosal toxicity, including apoptosis-regulating genes of the BCL2 family; up-regulation of c-Jun and c-Jun amino-terminal kinase, which in turn up-regulates NRF2; and production of proinframmatory cytokines, TNF-alpha, IL-1 beta, IL-6, the presence of which may cause damage to epithelium via reduced oxygenation and basal cell death, endothelium, and connective tissue; radiation and some cytotoxic agents also cause apoptosis via hydrolyzation of sphingomyelin (a cell-membrane lipid), a process that increases ceramide levels and results in cell apoptosis; fibroblasts in the submucosa may be damaged by radiation or chemotherapy, either directly or via stimulation of metalloproteinases. Phase 3, "the signal amplification phase," includes: a range of proteins that accumulate and target the submucosa, causing tissue damage and initiating a positive feedback loop, amplifying the primary damage caused by the radiation or chemotherapy. For example, a pathway that results in cell death is activated by TNF-α, which in turn activates NFκB and initiates mitogen-activated protein kinase (MAPK) signaling, in turn activating JNK (a member of the MAP kinase family), in turn regulating the activity of AP1. Cell death caused by this pathway occurs in the submucosa as well as the epithelium. TNF-α and IL-1β both induce matrix metalloproteinase activation. Phase 4, "the ulcerative phase," may include: functional trauma caused lesions (e.g., with respect to oral mucositis, the lesions appear in the mouth); excessive bacterial colonization of lesions, (e.g., with respect to oral mucositis, the bacterial colonization of lesions may be exacerbated by reduced salivary levels and poor oral hygiene as often happens in neutropenic patients); endotoxin released from gram-negative organisms and cell wall products from gram-positive bacteria may then interact with tissue macrophages to trigger release of further IL-1 and TNF-α, exacerbating mucosal damage. Secondary infections that result include fungal infections, viral infections and bacterial infections. Phase 5, "the healing phase," includes: cell proliferation and differentiation returns to normal; bone marrow recovery results in increased numbers of white cells and control of local infection.

An exemplary assay for the treatment of oral mucositis may be performed as described in the phase 3 clinical trial of Kepivance™ (palifermin) (see, Spielberger, *N. Engl. J. Med.*, 351(25):2590-2598 (2004)), or as described in phase II clinical trials of GM-CSF (molgramostin) (see McFleese et al., *Br. J. Radiol.* 79(943):608-13 (2006)).

As used herein, the phrase "active vitamin D compound" refers to a vitamin D compound that is or becomes biologically active when administered to a subject or contacted with cells. The biological activity of a vitamin D compound can be assessed by assays well known to one of skill in the art such as, e.g., immunoassays that measure the expression of a gene regulated by vitamin D. Vitamin D compounds exist in several forms with different levels of activity in the body. For example, a vitamin D compound may be partially activated by first undergoing hydroxylation in the liver at the carbon-25 position and then may be fully activated in the kidney by further hydroxylation at the carbon-1 position.

The prototypical active vitamin D compound is 1α,25-hydroxyvitamin D3, also known as calcitriol. The active vitamin D compound of the present invention may also be a partially hydroxylated vitamin D such as 1α-hydroxyvitamin D3, also known as 1α-calcidol, and 25-hydroxyvitamin D3, also known as calcifediol. A large number of other active vitamin D compounds are known and can be used in the practice of the invention.

The active vitamin D compounds of the present invention include analogs, homologs, mimics and derivatives of vitamin D compounds. The term "mimic" as used herein is intended to refer to non-secosteroidal vitamin D mimic compounds. In general, these non-secosteroidal vitamin D mimics are compounds that do not structurally fall within the class of compounds generally known as vitamin D compounds but which modulate the activity of vitamin D nuclear receptors. The active vitamin D compounds of the invention include, without limitation, the active vitamin D compounds, analogs, homologs derivatives and mimics disclosed in U.S. 2006/0178351 and WO2006/116204 (either directly or by reference to other publications).

As used herein, the phrase "an active vitamin D in combination with one or more therapeutic agents," refers to the combined administration of an active vitamin D compound (including homologs, derivatives or mimics thereof) one or more therapeutic agents, wherein the active vitamin D compound or the mimic thereof can be administered prior to, concurrently with, or after the administration of said one or more therapeutic agents.

Thus, the active vitamin D compounds of the invention include, without limitation, the vitamin D compounds, analogs, derivatives and mimics described in the following patents, each of which is incorporated by reference: U.S. Pat. Nos. 4,391,802 (1α-hydroxyvitamin D derivatives); 4,717,721 (1α-hydroxy derivatives with a 17 side chain greater in length than the cholesterol or ergosterol side chains); 4,851,401 (cyclopentano-vitamin D analogs); 4,866,048 and 5,145,846 (vitamin D3 analogues with alkynyl, alkenyl, and alkanyl side chains); 5,120,722 (trihydroxycalciferol); 5,547,947 (fluoro-cholecalciferol compounds); 5,446,035 (methyl substituted vitamin D); 5,411,949 (23-oxa-derivatives); 5,237,110 (19-nor-vitamin D compounds; 4,857,518 (hydroxylated 24-homo-vitamin D derivatives). Particular examples include ROCALTROL® (Roche Laboratories); CALCIJEX® injectable calcitriol; investigational drugs from Leo Pharmaceuticals including EB 1089 (24a,26a,27a-trihomo-22,24-diene-1αa,25-(OH)2-D3, KH 1060 (20-epi-22-oxa-24a,26a,27a-trihomo-1α,25-(OH)2-D3), MC 1288 (1,25-(OH)2-20-epi-D3) and MC 903 (calcipotriol, 1α24s-(OH)2-22-ene-26,27-dehydro-D3); Roche Pharmaceutical drugs that include 1,25-(OH)2-16-ene-D3,1,25-(OH)2-16-ene-23-yne-D3, and 25-(OH)2-16-ene-23-yne-D3; Chugai Pharmaceuticals 22-oxacalcitriol (22-oxa-1α,25-(OH)2-D3; 1a-(OH)-D5 from the University of Illinois; and drugs from the Institute of Medical Chemistry-Schering AG that include ZK 161422 (20-methyl-1,25-(OH)2-D3) and ZK 157202 (20-methyl-23-ene-1,25-(OH)2-D3); 1a-(OH)-D2; 1a-(OH)-D3 and 1a-(OH)-D4. Additional examples include 1α,25-(OH)2-26,27-d6-D3; 1α,25-(OH)2-22-ene-D3; 1α,25-(OH)2-D3, 1α,25-(OH)2-D2; 1α,25-(OH)2-D4; 1α,24,25-(OH)3-D3; 1α,24,25-(OH)3-D2; 1α,24,25-(OH) 3-D4; 1α-(OH)-25-FD3; 1α-(OH)-25-FD4; 1α-(OH)-25-FD2; 1α,24-(OH)2-D4; 1α,24-(OH)2-D3; 1α,24-(OH)2-D2; 1α,24-(OH)2-25-FD4; 1α,24-(OH)2-25-FD3; 1α,24-(OH)2-25-FD2; 1α,25-(OH)2-26,27-F6-22-ene-D3) 1α,25-(OH)2-26,27-F6-D3, 1α,25S—(OH)2-26-F3-D3; 1α,25-(OH)2~24-F2-D3, 1α,25S,26-(OH)2-22-ene-D3; 1α,25R,26-(OH)2-22-ene-D3; 1α,25-(OH)2-D2; 1α,25-(OH)2-24-epi-D3; 1α,25-(OH)2-23-yne-D3, 1α,25-(OH)2-24R-F-D3; 1α,25S,26-(OH)2-D3, 1α,24R—(OH)2-25F-D3; 1α,25-(OH)2-26,27-F6-23-yne-D3, 1α,25R—(OH)2-26-F3-D3, 1α,25,28-(OH)3-D2; 1α,25-(OH)2-16-ene-23-yne-D3>1α,24R,25-(OH)3-D3, 1α, 25-(OH)2-26,27-F6-23-ene-D3, 1α,25R—(OH)2-22-ene-26-F3-D3, 1α,25S—(OH)2-22-ene-26-F3-D3>1α,25R—(OH)2-D3-26,26,26-d3; 1α,25S—(OH)2-D3-26,26,26-d3; and 1α,25R—(OH)2-22-ene-D3-26,26,26-d3. Additional examples can be found in U.S. Pat. No. 6,521,608. See also, e.g., U.S. Pat. Nos. 6,503,893, 6,482,812, 6,441,207, 6,410,523, 6,399,797, 6,392,071, 6,376,480, 6,372,926, 6,372,731, 6,359,152, 6,329,357, 6,326,503, 6,310,226, 6,288,249, 6,281,249, 6,277,837, 6,218,430, 6,207,656, 6,197,982, 6,127,559, 6,103,709, 6,080,878, 6,075,015, 6,072,062, 6,043,385, 6,017,908, 6,017,907, 6,013,814, 5,994,332, 5,976,784, 5,972,917, 5,945,410, 5,939,406, 5,936,105, 5,932,565, 5,929,056, 5,919,986, 5,905,074, 5,883,271, 5,880,113, 5,877,168, 5,872,140, 5,847,173, 5,843,927, 5,840,938, 5,830,885, 5,824,811, 5,811,562, 5,786,347, 5,767,111, 5,756,733, 5,716,945, 5,710,142, 5,700,791, 5,665,716, 5,663,157, 5,637,742, 5,612,325, 5,589,471, 5,585,368, 5,583,125, 5,565,589, 5,565,442, 5,554,599, 5,545,633, 5,532,228, 5,508,392, 5,508,274, 5,478,955, 5,457,217, 5,447,924, 5,446,034, 5,414,098, 5,403,940, 5,384,313, 5,374,629, 5,373,004, 5,371,249, 5,430,196, 5,260,290, 5,393,749, 5,395,830, 5,250,523, 5,247,104, 5,397,775, 5,194,431, 5,281,731, 5,254,538, 5,232,836, 5,185,150, 5,321,018, 5,086,191, 5,036,061, 5,030,772, 5,246,925, 4,973,584, 5,354,744, 4,927,815, 4,804,502, 4,857,518, 4,851,401, 4,851,400, 4,847,012, 4,755,329, 4,940,700, 4,619,920, 4,594,192, 4,588,716, 4,564,474, 4,552,698, 4,588,528, 4,719,204, 4,719,205, 4,689,180, 4,505,906, 4,769,181, 4,502,991, 4,481,198, 4,448,726, 4,448,721, 4,428,946, 4,411,833, 4,367,177, 4,336,193, 4,360,472, 4,360,471, 4,307,231, 4,307,025, 4,358,406, 4,305,880, 4,279,826, and 4,248,791.

Examples of Vitamin D mimics include bis-aryl derivatives disclosed by U.S. Pat. No. 6,218,430 and WO publication 2005/037755. Additional examples of non-secosteroidal vitamin D mimic compounds suitable for the present invention can be found in U.S. Pat. No. 6,831,106; 6,706,725; 6,689, 922; 6,548,715; 6,288,249; 6,184,422, 6,017,907, 6,858,595 and 6,358,939.

In one aspect the invention is drawn to methods employing non-secosteroidal vitamin D mimic compounds disclosed in International Publication No. WO2006/074226, the contents of which are hereby incorporated by reference.

As used herein, the terms "treat", "treatment" or "treating" refer to the amelioration of one or more symptoms associated with mucositis.

As used herein, the phrase "therapeutically effective amount" with respect to an active vitamin D compound refers to an amount which provides a therapeutic benefit, including, the prevention, treatment or amelioration of mucositis. For example, in one embodiment, a therapeutically effective amount of a vitamin D compound refers to an amount sufficient to reduce mucositis by at least 15% or more (at least 20%, at least 30%, at least 40%, at least 50%, at least 60%, at least 70%, at least 80%, at least 90%) as measured by Radiation Injury Score or as measured by structural damage to a cell or tissue (e.g., presence, size, or duration of structural damage) or neutrophil infiltration. In another embodiment, a therapeutically effective amount of a vitamin D compound refers to an amount sufficient to reduce the grade of mucositis, using any mucositis grading scale, including without limitation, the grading scales described in the publication by Sonis et al., *Cancer Suppl.*, 100(9):1995-2025 (2004), the contents of which are hereby incorporated by reference.

In a preferred embodiment, mucositis is measured using a clinical scale developed or based on NCI, WHO or RTOG designs. See Sonis et al., *Cancer Suppl.*, 100(9):1995-2025 (2004).

The amount and frequency of administration of the active vitamin D compound will be regulated according to the judgment of the attending clinician considering such factors as age, condition and size of the patient as well as severity of the symptoms being treated. Factors such as the pharmaceutical agents being used and the route of administration could also be important.

In one embodiment the invention comprises administering the active vitamin D compound by high dose pulse administration. As used herein, the term "high dose pulse administration"( ) refers to a regimen of intermittent administration of an active vitamin D compound to a subject in a therapeutic effective amount without inducing severe symptomatic hypercalcaemia.

The term "hypercalcemia" as used herein refers to a medical condition in which the concentration of calcium ions in the plasma is greater than about 10.5 mg/dL in humans.

The term "symptomatic hypercalcemia" as used herein refers to symptoms associated with one or more of the signs or symptoms of hypercalcemia. Early manifestations of hypercalcemia include weakness, headache, somnolence, nausea, vomiting, dry mouth, constipation, muscle pain, bone pain, or metallic taste. Late manifestations include polydypsia, polyuria, weight loss, pancreatitis, photophobia, pruritis, renal dysfunction, aminotransferase elevation, hypertension, cardiac arrhythmias, psychosis, stupor, or coma. Methods to determine the concentration of calcium ions in blood plasma are generally within the capability of a person of ordinary skill in the art.

The term "severe symptomatic hypercalcemia" as used herein is referred to grade 3 or grade 4 toxic level of hypercalcemia as defined in U.S. Pat. No. 6,521,608, which is incorporated by reference herein in its entirety. A grade 4 toxicity is associated with reduced count for WBC, platelets, hemoglobin, neutrophils and lymphocytes; massive hemorrhage; gastrointestinal problems (such as vomiting more than 10 times a day, diarrhea (>10 times a day) and stomatitis which requires IV nutrition); hepatic failures (such as elevated bilirubin and hepatic coma), kidney/bladder dysfunction; cardiovascular events (such as refractory congestive heart failure, acute myocardial infraction, dyspnea at rest and cardiac tamponade); neuralgic disorders (such as paralysis, coma, seizures, cerebellar necrosis, severe headaches, blindness, uncorrectable deafness and suicidal mood) and metabolic problems (such as hyperglycemia (blood glucose>500 mg/dL) with ketoacidosis). Although grade 3 toxicity is milder than grade 4 toxicity, it can be life threatening and is associated with reduced count for WBC, platelets, hemoglobin, neutrophils and lymphocytes; gross hemorrhage; gastrointestinal problems (such as vomiting 6-10 times a day, diarrhea (7-9 times a day) and painful ulcers (patient cannot eat)); hepatic failures (such as precoma and elevated bilirubin); cardiovascular events (such as mild congestive heart failure responsive to treatment, angina without infraction and symptomatic effusion); neurologic disorders (such as severe loss or impairment of neurosensory, severe cortical contusion, unrelenting headache and correctable hearing loss) and weight change.

In a preferred embodiment of the invention, the active vitamin D compound has a reduced hypercalcemic effect as compared to vitamin D so that increased doses of the compound can be administered without inducing hypercalcemia in the subject. A reduced hypercalcemic effect is defined as an effect which is less than the hypercalcemic effect induced by administration of an equal dose of 1α,25-hydroxyvitamin D3 (calcitriol). As an example, EB 1089 has a hypercalcemic effect which is 50% of the hypercalcemic effect of calcitriol. Additional active vitamin D compounds having a reduced hypercalcemic effect include Ro23-7553 and Ro24-5531 available from Hoffmann LaRoche. Other examples of active vitamin D compounds having a reduced hypercalcemic effect can be found in U.S. Pat. No. 4,717,721. Determining the hypercalcemic effect of an active vitamin D compound is routine in the art and can be carried out as disclosed in Hansen et al., *Curr. Pharm. Des.* (5:803-828 (2000)).

The active vitamin D compound is preferably administered at a dose of about 0.1 µg to about 10 mg, e.g., about 0.5 µg to about 1 mg, or from about 15 µg to about 500 µg. In a specific embodiment, an effective amount of an active vitamin D compound is 0.5, 1, 2, 3, 4, 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 350, 400, 450, 500, 550, 600, 650, 700, 750, 800, 850, 900, 950, 1000, 2000, 3000, 4000, 5000, 6000, 7000, 8000, 9000, or 10000 µg or more. In certain embodiments, an effective dose of an active vitamin D compound is between about 3 µg to about 1 mg, e.g., between about 7 µg to about 1 mg, between 15 µg to about 1 mg, between about 15 µg to about 300 µg, between about 15 µg to about 200 µg, between about 15 µg to about 100 µg, between about 15 µg to about 60 µg, between about 15 µg to about 45 µg, between about 30 µg to about 60 µg, or about 45 µg. In certain embodiments, the methods of the invention comprise administering an active vitamin D compound in a dose of about 0.12 µg/kg bodyweight to about 200 µg/kg bodyweight.

If the active vitamin D compound is to be administered daily, the dose may be kept low, for example about 0.5 µg to about 5 µg, in order to avoid or diminish the induction of hypercalcemia. If the active vitamin D compound has a reduced hypercalcemic effect a higher daily dose may be administered without resulting in hypercalcemia, for example about 10 µg to about 20 µg or higher (up to about 50 µg to about 100 µg).

In a preferred embodiment of the invention, the active vitamin D compound is administered by HDPA so that high doses of the active vitamin D compound can be administered without inducing severe symptomatic hypercalcemia. The frequency of the HDPA can be limited by a number of factors including, but not limited to, the pharmacokinetic parameters of the compound or formulation and the pharmacodynamic effects of the active vitamin D compound on the subject. For example, subjects having impaired renal function may require less frequent administration of the active vitamin D compound because of the decreased ability of those subjects to excrete calcium.

The following is exemplary only and merely serves to illustrate that the term HDPA can encompass any discontinuous administration regimen designed by a person of skill in the art.

In one example, the active vitamin D compound can be administered not more than once every three days, every four days, every five days, every six days, every seven days, every eight days, every nine days, or every ten days. The administration can continue for one, two, three, or four weeks or one, two, or three months, or longer. Optionally, after a period of rest, the active vitamin D compound can be administered under the same or a different schedule. The period of rest can be one, two, three, or four weeks, or longer, according to the pharmacodynamic effects of the active vitamin D compound on the subject.

In another example, the active vitamin D can be administered once per week for three months.

In a preferred embodiment, the vitamin D compound can be administered once per week for three weeks of a four week cycle. After a one week period of rest, the active vitamin D compound can be administered under the same or different schedule.

Further examples of dosing schedules that can be used in the methods of the present invention are provided in U.S. Pat. No. 6,521,608, which is incorporated by reference in its entirety.

The above-described administration schedules are provided for illustrative purposes only and should not be considered limiting. A person of skill in the art will readily understand that all active vitamin D compounds, derivatives, homologs and mimics thereof are within the scope of the invention and that the exact dosing and schedule of administration of these compounds can vary due to many factors.

The amount of a therapeutically effective dose of a pharmaceutical agent in the acute or chronic management of a disease or disorder may differ depending on factors including, but not limited to, the disease or disorder treated, the specific pharmaceutical agents, formulations thereof, dosing regimens and the route of administration. The dose, dose frequency, duration, or any combination thereof, may also vary according to age, gender, body weight, response, and the past medical history of the subject as well as the route of administration, pharmacokinetics, and pharmacodynamic effects of the pharmaceutical agents. These factors are routinely considered by one of skill in the art.

The rate of absorption and clearance of vitamin D compounds are affected by a variety of factors that are well known to persons of skill in the art. As discussed above, the pharmacokinetic properties of active vitamin D compounds limit the peak concentration of vitamin D compounds that can be obtained in the blood without inducing the onset of hypercalcemia. The rate and extent of absorption, distribution, binding or localization in tissues, biotransformation, and excretion of the active vitamin D compound can all affect the frequency at which the pharmaceutical agents can be administered.

In one embodiment of the invention, an active vitamin D compound is administered at a dose sufficient to achieve peak plasma concentrations of the active vitamin D compound of about 0.1 nM to about 1000 nM, e.g., about 0.1 nM to about 20 nM. In certain embodiments, the methods of the invention comprise administering the active vitamin D compound in a dose that achieves peak plasma concentrations of 0.1 nM, 0.2 nM, 0.3 nM, 0.4 nM, 0.5 nM, 0.6 nM, 0.7 nM, 0.8 nM, 0.9 nM, 1 nM, 2 nM, 3 nM, 4 nM, 5 nM, 6 nM, 7 nM, 8 nM, 9 nM, 10 nM, 12.5 nM, 15 nM, 17.5 nM 20 nM, 22.5 nM, 25 nM, 30 nM, 35 nM, 40 nM, 45 nM, 50 nM, 60 nM, 70 nM, 80 nM, 90 nM, 100 nM, 150 nM, 200 nM, 250 nM, 300 nM, 350 nM, 400 nM, 450 nM, 500 nM, 550 nM, 600 nM, 650 nM, 700 nM, 750 nM, 800 nM, 850 nM, 900 nM, 950 nM or 1000 nM or any range of concentrations therein. In other embodiments, the active vitamin D compound is administered in a dose that achieves peak plasma concentrations of the active vitamin D compound exceeding about 0.25 nM, e.g., about 0.25 nM to about 100 nM, about 0.25 nM to about 20 nM, about 0.25 nM to about 10 nM, about 0.25 nM to about 2.5 nM. In other embodiments, the active vitamin D compound is administered in a dose that achieves peak plasma concentrations of the active vitamin D compound exceeding about 0.5 nM, e.g., about 0.5 nM to about 100 nM, about 0.5 nM to about 20 nM, about 0.5 nM to about 10 nM, about 0.5 nM to about 2.5 nM. In other embodiments, the active vitamin D compound is administered in a dose that achieves peak plasma concentrations of the active vitamin D compound exceeding about 1 nM, e.g., about 1 nM to about 100 nM, about 1 nM to about 20 nM, about 1 nM to about 10 nM, about 1 nM to about 7 nM, or about 3 nM to about 5 nM.

In another preferred embodiment, the active vitamin D compound is administered at a dose of at least about 0.010 µg/kg bodyweight, more preferably about 0.12 µg/kg bodyweight, and more preferably at a dose of at least about 0.5 µg/kg bodyweight.

One of skill in the art will recognize that these standard doses are for an average sized adult of approximately 70 kg and can be adjusted for the factors routinely considered as stated above.

In certain embodiments, the methods of the invention further comprise administering a dose of an active vitamin D compound that achieves peak plasma concentrations rapidly, e.g., within four hours. In further embodiments, the methods of the invention comprise administering a dose of an active vitamin D compound that is eliminated quickly, e.g., with an elimination half-life of less than 12 hours.

While obtaining high concentrations of the active vitamin D compound is beneficial, it must be balanced with clinical safety, e.g., hypercalcemia. Thus, in one aspect of the invention, the methods of the invention encompass HDPA of active vitamin D compounds to a subject having mucositis or at risk of developing mucositis and monitoring the subject for symptoms associated with hypercalcemia. Such symptoms include calcification of soft tissues (e.g., cardiac tissue), increased bone density, and hypercalcemic nephropathy.

In certain embodiments, high blood levels of vitamin D compounds can be safely obtained in conjunction with reducing the transport of calcium into the blood. In one embodiment, higher concentrations of active vitamin D compound are safely obtainable without the onset of hypercalcemia when the vitamin D compound is administered in conjunction with a reduced calcium diet. In one example, the calcium can be trapped by an adsorbent, absorbent, ligand, chelate, or other binding moiety that cannot be transported into the blood through the small intestine. In another example, the rate of osteoclast activation can be inhibited by administering, for example, a bisphosphonate such as, e.g., zoledronate, pamidronate, or alendronate, or a corticosteroid such as, e.g., dexamethasone or prednisone, in conjunction with the active vitamin D compound.

In certain embodiments, high blood levels of active vitamin D compounds are safely obtained in conjunction with maximizing the rate of clearance of calcium. In one example, calcium excretion can be increased by ensuring adequate hydration and salt intake. In another example, diuretic therapy can be used to increase calcium excretion.

The doses of the vitamin D analogs and vitamin D mimics may be adjusted proportionate to the ratio of the efficacy index to the calcemic index according to the formula: Dose=Calcitriol Dose×(EI/CI) where Dose is the analog or mimic dose, calcitriol Dose is calcitriol dose, EI is the analog or mimic efficacy index and CI is the analog or mimic calcemic index, wherein the term "efficacy index" is the ratio of the concentration of the vitamin D analog or mimic to the concentration of calcitriol at equivalent potency. Thus, the efficacy index is a fraction less than one when the vitamin D analog or mimic is less potent than calcitriol. EI is number greater than one when calcitriol is less potent than the vitamin D analog or mimic. The "calcemic index" of a drug is a measure of the relative ability of the drug to generate a calcemic response as reported in Bouillon et al., *Endocrine Reviews* 16:200-257, 1995. A calcemic index of 1 corresponds to the relative calcemic activity of calcitriol. A calcemic index of about 0.01 corresponds to the calcemic activity of a drug with approximately 100 times less calcemic activity than calcitriol. A calcemic index of 0.5 would correspond to a drug having approximately half the calcemic activity of calcitriol. The calcemic index of a drug can vary depending on the assay conducted, e.g. whether one is measuring stimulation of intestinal calcium absorption (a process by which dietary calcium enters into the physiological processes to contribute to the skeletal growth of the organism and to the maintenance of calcium homeostasis) or bone calcium mobilizing activity (a process by which the bone matrix acts as an exchangeable reservoir for calcium). See U.S. Pat. No. 6,521,608 for further detail.

The active vitamin D compound may be administered by various routes including but not limited to, oral (p.o.), intramuscular (i.m.), intravenous (i.v.), intraperitoneal (i.p.), intravascular (i.v.), subcutaneous (s.c.), or intrathecal (i.t.), parenteral, rectal, nasal, topical, or transdermal routes of administration.

In a preferred embodiment the active vitamin D compound is administered orally. In another preferred embodiment, the active vitamin D compound will be administered systemically.

Combination Treatment

In certain embodiments, the invention encompasses the use of an active vitamin D compound (including homologs, derivatives or mimics thereof) in combination with one or more therapeutic agents or therapeutic regimens to treat or prevent mucositis.

The active vitamin D compound can be administered prior to (e.g., 0.5 hours, 1 hour, 2 hours, 4 hours, 6 hours, 12 hours, 24 hours, 36 hours, 2 days, 3 days, 4 days, 5 days, 6 days, 7 days, 2 weeks, 3 weeks, 4 weeks or more), concurrently with, or after (e.g., 0.5 hours, 1 hour, 2 hours, 4 hours, 6 hours, 12 hours, 24 hours, 36 hours, 2 days, 3 days, 4 days, 5 days, 6 days, 7 days, 2 weeks, 3 weeks, 4 weeks or more) the administration of one or more therapeutic agents or therapeutic regimens.

In certain embodiments, the method of administering an active vitamin D compound in combination with one or more therapeutic agents may be repeated at least once. The method may be repeated as many times as necessary to achieve or maintain a therapeutic response, e.g., from one to about ten times. With each repetition of the method the active vitamin D compound and the one or more therapeutic agents may be the same or different from that used in the previous repetition. Additionally, the time period of administration of the active vitamin D compound and the manner in which it is administered (i.e., daily or HDPA) can vary from repetition to repetition.

The active vitamin D compound can be administered in combination with any other therapeutic agent or therapeutic regimen that can prevent or treat mucositis. Agents that could be used to treat or prevent mucositis are known in the art.

In one embodiment, the active vitamin D compound is administered in combination with an anti-fungal, an anti-bacterial, an anti-viral, an anesthetic or a gastrointestinal agent. In one embodiment, the active vitamin D compound is administered with a mouthwash or an oral care product. In one embodiment, the active vitamin D compound is administered with an immunomodulatory agent.

In one embodiment, the active vitamin D compound can be administered in combination with cryotherapy, mouthrinse or mouthwash, keratinocyte growth factor, GM-CSF (molgramostin), transforming growth factor 3, amifostin, PAR-1 inhibitors, Kepivance™ (palifermin) (Spielberger, *N Engl J Med*, 351(25):2590-2598 (2004)), amifostin (Dunst et al., *Strahlenther Onkol*, 176(9):416-421 (2000)), glutamine or L-glutamine (Blijlevens et al., *Support Care Cancer*, 13(10): 790-796 (2005); Aquino et al., *Bone Marrow Transplant*, 36(7):611-616 (2005); and U.S. Pat. No. 5,438,075), teduglutide (Booth et al., *Cell Prolif*, 37(6):385-400 (2004)), sucralfate mouth rinses (Makkonen et al., Int *J Radiat Oncol Biol Phys*, 30(1):177-182 (1994)), iseganan (Cole and Waring, *Am J Respir Med*, 1(4):249-259 (2002)), lactoferrin (Van't Land et al., *Dig Dis Sci*, 49(3):425-433 (2004)), mesna (Ypsilantis et al., *J Surg Res*, 121(1):84-91 (2004)), trefoil factor (Beck et al., *Gastroenterology*, 126(3):796-808 (2004); and Xian et al., *Am J Physiol*, 277(4 Pt 1):G785-975 (1999)), CASAD (calcium alumino-silicate anti-diarrheal from NewCo Pharmaceuticals LLC), or a combination of two or more of the above.

As used herein, the phrase "protease activated receptor-1 inhibitor" also referred to herein as "PAR-1," means an agent that inhibits signaling from protease activated receptor-1. In one embodiment, the PAR-1 inhibitor is selected from the group of PAR-inhibitors disclosed in U.S. Provisional Application No. 60/751,820, the disclosure of which is hereby incorporated by reference.

In some embodiments, the administration of the active vitamin D compound reduces the dosage and/or frequency of administration of one or more dosages of the therapeutic agents to be used in combination with the active vitamin D compound.

In one embodiment of the invention, an active vitamin D compound is administered to a subject in need thereof before, during and/or after radiation therapy or chemotherapy. The active vitamin D compound can be administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, or more prior to the radiation therapy or chemotherapy. The active vitamin D compound can be administered 1 hour, 2 hours, 3 hours, 4 hours, 5 hours, 6 hours, 12 hours, 1 day, 2 days, 3 days, 4 days, 5 days, 6 days, 1 week, 2 weeks, 3 weeks, 4 weeks, or more after the radiation therapy or chemotherapy. The administration of the active vitamin D compound can be continued for up to six months after the radiation therapy or chemotherapy.

Pharmaceutical Compositions

The active vitamin D compound (including homologs, derivatives and mimics thereof) may be administered as part of a pharmaceutical composition comprising a pharmaceutically acceptable carrier, wherein the active vitamin D compound is present in an amount which is effective to achieve its intended purpose, i.e., to treat or prevent mucositis. The pharmaceutical composition may further comprise one or more excipients, diluents or any other components known to persons of skill in the art and germane to the methods of formulation of the present invention. The pharmaceutical composition may additionally comprise other compounds typically used as adjuncts during prevention, treatment, or amelioration of mucositis.

The term "pharmaceutical composition" as used herein is to be understood as defining compositions of which the individual components or ingredients are themselves pharmaceutically acceptable, e.g., where oral administration is foreseen, acceptable for oral use.

The pharmaceutical composition can be prepared in single unit dosage forms. The dosage forms are suitable for oral, mucosal (nasal, sublingual, vaginal, buccal, rectal), parenteral (intravenous, intramuscular, intraarterial), or topical administration. Preferred dosage forms of the present invention include oral dosage forms and intravenous dosage forms.

Examples of pharmaceutical compositions that could be used in the claimed invention are known in the art and include those described in US Publication Nos. 2006/0189586, 2006/0178351 and PCT Publication No. WO2006/116204, the contents of which are hereby incorporated by reference.

Intravenous forms include, but are not limited to, bolus and drip injections. In preferred embodiments, the intravenous dosage forms are sterile or capable of being sterilized prior to administration to a subject since they typically bypass the subject's natural defenses against contaminants. Examples of intravenous dosage forms include, but are not limited to, Water for Injection USP; aqueous vehicles including, but not limited to, Sodium Chloride Injection, Ringer's Injection, Dextrose Injection, Dextrose and Sodium Chloride Injection, and Lactated Ringer's Injection; water-miscible vehicles including, but not limited to, ethyl alcohol, polyethylene glycol and polypropylene glycol; and non-aqueous vehicles including, but not limited to, corn oil, cottonseed oil, peanut oil, sesame oil, ethyl oleate, isopropyl myristate and benzyl benzoate.

In a preferred embodiment of the invention, the pharmaceutical compositions comprising active vitamin D compounds are emulsion pre-concentrate formulations. The compositions of the invention meet or substantially reduce the difficulties associated with active vitamin D compound therapy hitherto encountered in the art including, in particular, undesirable pharmacokinetic parameters of the compound upon administration to a patient.

According to one aspect of the present invention, a pharmaceutical composition is provided comprising (a) a lipophilic phase component, (b) one or more surfactants, (c) an active vitamin D compound; wherein said composition is an emulsion pre-concentrate, which upon dilution with water, in a water to composition ratio of about 1:1 or more of said water, forms an emulsion having an absorbance of greater than 0.3 at 400 nm. The pharmaceutical composition of the invention may further comprise a hydrophilic phase component.

In another aspect of the invention, a pharmaceutical emulsion composition is provided comprising water (or other aqueous solution) and an emulsion pre-concentrate.

The term "emulsion pre-concentrate," as used herein, is intended to mean a system capable of providing an emulsion upon contacting with, e.g., water. The term "emulsion," as used herein, is intended to mean a colloidal dispersion comprising water and organic components including hydrophobic (lipophilic) organic components. The term "emulsion" is intended to encompass both conventional emulsions, as understood by those skilled in the art, as well as "sub-micron droplet emulsions," as defined immediately below. The term "sub-micron droplet emulsion," as used herein is intended to mean a dispersion comprising water and organic components including hydrophobic (lipophilic) organic components, wherein the droplets or particles formed from the organic components have an average maximum dimension of less than about 1000 nm.

Sub-micron droplet emulsions are identifiable as possessing one or more of the following characteristics. They are formed spontaneously or substantially spontaneously when their components are brought into contact, that is without substantial energy supply, e.g., in the absence of heating or the use of high shear equipment or other substantial agitation. They exhibit thermodynamic stability and they are monophasic.

The particles of a sub-micron droplet emulsion may be spherical, though other structures are feasible, e.g. liquid crystals with lamellar, hexagonal or isotropic symmetries. Generally, sub-micron droplet emulsions comprise droplets or particles having a maximum dimension (e.g., average diameter) of between about 50 nm to about 1000 nm, and preferably between about 200 nm to about 300 nm.

The pharmaceutical compositions of the present invention will generally form an emulsion upon dilution with water. The emulsion will form according to the present invention upon the dilution of an emulsion pre-concentrate with water in a water to composition ratio of about 1:1 or more of said water. According to the present invention, the ratio of water to composition can be, e.g., between 1:1 and 5000:1. For example, the ratio of water to composition can be about 1:1, 2:1, 3:1, 4:1, 5:1, 10:1, 200:1, 300:1, 500:1, 1000:1, or 5000:1. The skilled artisan will be able to readily ascertain the particular ratio of water to composition that is appropriate for any given situation or circumstance.

According to the present invention, upon dilution of said emulsion pre-concentrate with water, an emulsion will form having an absorbance of greater than 0.3 at 400 nm. The absorbance at 400 nm of the emulsions formed upon 1:100 dilution of the emulsion pre-concentrates of the present invention can be, e.g., between 0.3 and 4.0. For example, the absorbance at 400 nm can be about 0.4, 0.5, 0.6, 1.0, 1.2, 1.6, 2.0, 2.2, 2.4, 2.5, 3.0, or 4.0. Methods for determining the absorbance of a liquid solution are well known by those in the art. The skilled artisan will be able to ascertain and adjust the relative proportions of the ingredients of the emulsion pre-concentrates of the invention in order to obtain, upon dilution with water, an emulsion having any particular absorbance encompassed within the scope of the invention.

The pharmaceutical compositions of the present invention can be, e.g., in a solid, semi-solid, or liquid formulation. Semi-solid formulations of the present invention can be any semi-solid formulation known by those of ordinary skill in the art, including, e.g., gels, pastes, creams and ointments.

The pharmaceutical compositions of the present invention comprise a lipophilic phase component. Suitable components for use as lipophilic phase components include any pharmaceutically acceptable solvent which is non-miscible with water. Such solvents will appropriately be devoid or substantially devoid of surfactant function.

The lipophilic phase component may comprise mono-, di- or triglycerides. Mono-, di- and triglycerides that may be used within the scope of the invention include those that are derived from C6, C8, C10, C12, C14, C16, C18, C20 and C22 fatty acids. Exemplary diglycerides include, in particular, diolein, dipalmitolein, and mixed caprylm-caprin diglycerides. Preferred triglycerides include vegetable oils, fish oils, animal fats, hydrogenated vegetable oils, partially hydrogenated vegetable oils, synthetic triglycerides, modified triglycerides, fractionated triglycerides, medium and long-chain triglycerides, structured triglycerides, and mixtures thereof.

Among the above-listed triglycerides, preferred triglycerides include: almond oil; babassu oil; borage oil; blackcurrant seed oil; canola oil; castor oil; coconut oil; corn oil; cottonseed oil; evening primrose oil; grapeseed oil; groundnut oil; mustard seed oil; olive oil; palm oil; palm kernel oil; peanut oil; rapeseed oil; safflower oil; sesame oil; shark liver oil; soybean oil; sunflower oil; hydrogenated castor oil; hydrogenated coconut oil; hydrogenated palm oil; hydrogenated soybean oil; hydrogenated vegetable oil; hydrogenated cottonseed and castor oil; partially hydrogenated soybean oil; partially soy and cottonseed oil; glyceryl tricaproate; glyceryl tricaprylate; glyceryl tricaprate; glyceryl triundecanoate; glyceryl trilaurate; glyceryl trioleate; glyceryl trilinoleate; glyceryl trilinolenate; glyceryl tricaprylate/caprate; glyceryl tricaprylate/caprate/laurate; glyceryl tricaprylate/caprate/linoleate; and glyceryl tricaprylate/caprate/stearate.

A preferred triglyceride is the medium chain triglyceride available under the trade name LABRAFAC CC. Other preferred triglycerides include neutral oils, e.g., neutral plant oils, in particular fractionated coconut oils such as known and commercially available under the trade name MIGLYOL, including the products: MIGLYOL 810; MIGLYOL 812; MIGLYOL 818; and CAPTEX 355.

Also suitable are caprylic-capric acid triglycerides such as known and commercially available under the trade name MYRITOL, including the product MYRITOL 813. Further suitable products of this class are CAPMUL MCT, CAPTEX 200, CAPTEX 300; CAPTEX 800, NEOBEE M5 and MAZOL 1400.

Especially preferred as lipophilic phase component is the product MIGLYOL 812. (See U.S. Pat. No. 5,342,625).

Pharmaceutical compositions of the present invention may further comprise a hydrophilic phase component. The hydrophilic phase component may comprise, e.g., a pharmaceutically acceptable C1-5 alkyl or tetrahydrofurfuryl di- or partial-ether of a low molecular weight mono- or poly-oxy-alkanediol. Suitable hydrophilic phase components include, e.g., di- or partial-, especially partial-, -ethers of mono- or poly-, especially mono- or di-, -oxy-alkanediols comprising from 2 to 12, especially 4 carbon atoms. Preferably the mono- or poly-oxy-alkanediol moiety is straight-chained. Exemplary hydrophilic phase components for use in relation to the present invention are those known and commercially available under the trade names TRANSCUTOL and COLYCOFUROL. (See U.S. Pat. No. 5,342,625).

In an especially preferred embodiment, the hydrophilic phase component comprises 1,2-propyleneglycol.

The hydrophilic phase component of the present invention may of course additionally include one or more additional ingredients. Preferably, however, any additional ingredients will comprise materials in which the active vitamin D compound is sufficiently soluble, such that the efficacy of the hydrophilic phase as a carrier medium for an active vitamin D compound is not materially impaired. Examples of possible additional hydrophilic phase components include lower (e.g., C1-5) alkanols, in particular ethanol.

Pharmaceutical compositions of the present invention also comprise one or more surfactants. Surfactants that can be used in conjunction with the present invention include hydrophilic or lipophilic surfactants, or mixtures thereof. Especially preferred are non-ionic hydrophilic and non-ionic lipophilic surfactants.

Suitable hydrophilic surfactants include reaction products of natural or hydrogenated vegetable oils and ethylene glycol, i.e. polyoxyethylene glycolated natural or hydrogenated vegetable oils, for example polyoxyethylene glycolated natural or hydrogenated castor oils. Such products may be obtained in known manner, e.g., by reaction of a natural or hydrogenated castor oil or fractions thereof with ethylene oxide, e.g., in a molar ratio of from about 1:35 to about 1:60, with optional removal of free polyethyleneglycol components from the product, e.g., in accordance with the methods disclosed in German Auslegeschriften 1,182,388 and 1,518,819.

Suitable hydrophilic surfactants for use in the present pharmaceutical compounds also include polyoxyethylene-sorbitan-fatty acid esters, e.g., mono- and trilauryl, palmityl, stearyl and oleyl esters, e.g., of the type known and commercially available under the trade name TWEEN; including the products: TWEEN 20 (polyoxyethylene(20)sorbitanmonolaurate), TWEEN 40 (polyoxyethylene(20)sorbitanmonopalmitate), TWEEN 60 (polyoxyethylene(20)sorbitanmonostearate), TWEEN 80 (polyoxyethylene(20)sorbitanmonooleate), TWEEN 65 (polyoxyethylene(20)sorbitantristearate), TWEEN 85 (polyoxyethylene(20)sorbitantrioleate), TWEEN 21 (polyoxyethylene(4)sorbitanmonolaurate), TWEEN 61 (polyoxyethylene(4)sorbitanmonostearate), and TWEEN 81 (polyoxyethylene(5)sorbitanmonooleate).

Especially preferred products of this class for use in the compositions of the invention are the above products TWEEN 40 and TWEEN 80. (See U.S. Pat. No. 5,342,625).

Also suitable as hydrophilic surfactants for use in the present pharmaceutical compounds are polyoxyethylene alkylethers; polyoxyethylene glycol fatty acid esters, for example polyoxyethylene stearic acid esters; polyglycerol fatty acid esters; polyoxyethylene glycerides; polyoxyethylene vegetable oils; polyoxyethylene hydrogenated vegetable oils; reaction mixtures of polyols and, e.g., fatty acids, glycerides, vegetable oils, hydrogenated vegetable oils, and sterols; polyoxyethylene-polyoxypropylene co-polymers; polyoxyethylene-polyoxypropylene block co-polymers; dioctylsuccinate, dioctylsodiumsulfosuccinate, di[2-ethylhexyl]-succinate or sodium lauryl sulfate; phospholipids, in particular lecithins such as, e.g., soya bean lecithins; propylene glycol mono- and di-fatty acid esters such as, e.g., propylene glycol dicaprylate, propylene glycol dilaurate, propylene glycol hydroxystearate, propylene glycol isostearate, propylene glycol laurate, propylene glycol ricinoleate, propylene glycol stearate, and, especially preferred, propylene glycol caprylic-capric acid diester; and bile salts, e.g., alkali metal salts, for example sodium taurocholate.

Suitable lipophilic surfactants include alcohols; polyoxyethylene alkylethers; fatty acids; bile acids; glycerol fatty acid esters; acetylated glycerol fatty acid esters; lower alcohol fatty acids esters; polyethylene glycol fatty acids esters; polyethylene glycol glycerol fatty acid esters; polypropylene glycol fatty acid esters; polyoxyethylene glycerides; lactic acid esters of mono/diglycerides; propylene glycol diglycerides; sorbitan fatty acid esters; polyoxyethylene sorbitan fatty acid esters; polyoxyethylene-polyoxypropylene block copolymers; trans-esterified vegetable oils; sterols; sugar esters; sugar ethers; sucroglycerides; polyoxyethylene vegetable oils; polyoxyethylene hydrogenated vegetable oils; reaction mixtures of polyols and at least one member of the group consisting of fatty acids, glycerides, vegetable oils, hydrogenated vegetable oils, and sterols; and mixtures thereof.

Suitable lipophilic surfactants for use in the present pharmaceutical compounds also include trans-esterification products of natural vegetable oil triglycerides and polyalkylene polyols. Such trans-esterification products are known in the art and may be obtained e.g., in accordance with the general procedures described in U.S. Pat. No. 3,288,824. They include trans-esterification products of various natural (e.g., non-hydrogenated) vegetable oils for example, maize oil, kernel oil, almond oil, ground nut oil, olive oil and palm oil and mixtures thereof with polyethylene glycols, in particular polyethylene glycols having an average molecular weight of from 200 to 800. Preferred are products obtained by trans-esterification of 2 molar parts of a natural vegetable oil triglyceride with one molar part of polyethylene glycol (e.g., having an average molecular weight of from 200 to 800). Various forms of trans-esterification products of the defined class are known and commercially available under the trade name LABRAFIL.

Additional lipophilic surfactants that are suitable for use with the present pharmaceutical compositions include oil-soluble vitamin derivatives, e.g., tocopherol PEG-1000 succinate ("vitamin E TPGS").

Also suitable as lipophilic surfactants for use in the present pharmaceutical compounds are mono-, di- and mono/di-glycerides, especially esterification products of caprylic or capric acid with glycerol; sorbitan fatty acid esters; pentaerythritol fatty acid esters and polyalkylene glycol ethers, for example pentaerythrite-dioleate, -distearate, -monolaurate, -polyglycol ether and -monostearate as well as pentaerythrite-fatty acid esters; monoglycerides, e.g., glycerol monooleate, glycerol monopalmitate and glycerol monostearate; glycerol triacetate or (1,2,3)-triacetin; and sterols and derivatives thereof, for example cholesterols and derivatives thereof, in particular phytosterols, e.g., products comprising sitosterol, campesterol or stigmasterol, and ethylene oxide adducts thereof, for example soya sterols and derivatives thereof.

It is understood by those of ordinary skill in the art that several commercial surfactant compositions contain small to moderate amounts of triglycerides, typically as a result of incomplete reaction of a triglyceride starting material in, for example, a trans-esterification reaction. Thus, the surfactants that are suitable for use in the present pharmaceutical compositions include those surfactants that contain a triglyceride. Examples of commercial surfactant compositions containing triglycerides include some members of the surfactant families available under the tradenames GELUCIRES, MAISINES, and MWITORS. Specific examples of these compounds are GELUCIRE 44/14 (saturated polyglycolized glycerides); GELUCIRE 50/13 (saturated polyglycolized glycerides); GELUCIRE 53/10 (saturated polyglycolized glycerides); GELUCIRE 33/01 (semi-synthetic triglycerides of Cs-C] g saturated fatty acids); GELUCIRE 39/01 (semi-synthetic glycerides); other GELUCIRES, such as 37/06, 43/01, 35/10, 37/02, 46/07, 48/09, 50/02, 62/05, etc.; MAISINE 35-1 (linoleic glycerides); and IMWITOR 742 (caprylic/capric glycerides). (See U.S. Pat. No. 6,267,985).

Still other commercial surfactant compositions having significant triglyceride content are known to those skilled in the art. It should be appreciated that such compositions, which contain triglycerides as well as surfactants, may be suitable to provide all or part of the lipophilic phase component of the present invention, as well as all or part of the surfactants.

The relative proportion of ingredients in the compositions of the invention will, of course, vary considerably depending on the particular type of composition concerned. The relative proportions will also vary depending on the particular function of ingredients in the composition. The relative proportions will also vary depending on the particular ingredients employed and the desired physical characteristics of the product composition, e.g., in the case of a composition for topical use, whether this is to be a free flowing liquid or a paste. Determination of workable proportions in any particular instance will generally be within the capability of a person of ordinary skill in the art. All indicated proportions and relative weight ranges described below are accordingly to be understood as being indicative of preferred or individually inventive teachings only and not as limiting the invention in its broadest aspect.

The lipophilic phase component of the invention will suitably be present in an amount of from about 30% to about 90% by weight based upon the total weight of the composition. Preferably, the lipophilic phase component is present in an amount of from about 50% to about 85% by weight based upon the total weight of the composition.

The surfactant or surfactants of the invention will suitably be present in an amount of from about 1% to 50% by weight based upon the total weight of the composition. Preferably, the surfactant(s) is present in an amount of from about 5% to about 40% by weight based upon the total weight of the composition.

The amount of active vitamin D compound in compositions of the invention will of course vary, e.g., depending on the intended route of administration and to what extent other components are present. In general, however, the active vitamin D compound of the invention will suitably be present in an amount of from about 0.005% to 20% by weight based upon the total weight of the composition. Preferably, the active vitamin D compound is present in an amount of from about 0.01% to 15% by weight based upon the total weight of the composition.

The hydrophilic phase component of the invention will suitably be present in an amount of from about 2% to about 20% by weight based upon the total weight of the composition. Preferably, the hydrophilic phase component is present in an amount of from about 5% to 15% by weight based upon the total weight of the composition.

The pharmaceutical composition of the invention may be in a semisolid formulation. Semisolid formulations within the scope of the invention may comprise, e.g., a lipophilic phase component present in an amount of from about 60% to about 80% by weight based upon the total weight of the composition, a surfactant present in an amount of from about 5% to about 35% by weight based upon the total weight of the composition, and an active vitamin D compound present in an amount of from about 0.01% to about 15% by weight based upon the total weight of the composition.

The pharmaceutical compositions of the invention may be in a liquid formulation. Liquid formulations within the scope of the invention may comprise, e.g., a lipophilic phase component present in an amount of from about 50% to about 60% by weight based upon the total weight of the composition, a surfactant present in an amount of from about 4% to about 25% by weight based upon the total weight of the composition, an active vitamin D compound present in an amount of from about 0.01% to about 15% by weight based upon the total weight of the composition, and a hydrophilic phase component present in an amount of from about 5% to about 10% by weight based upon the total weight of the composition.

Additional compositions that may be used include the following, wherein the percentage of each component is by weight based upon the total weight of the composition excluding the active vitamin D compound:

GELUCIRE 44/14 (about 50%); MIGLYOL 812 (about 50%)
GELUCIRE 44/14 (about 50%); Vitamin E TPGS (about 10%); MIGLYOL 812 (about 40%)
GELUCIRE 44/14 (about 50%); Vitamin E TPGS (about 20%); MIGLYOL 812 (about 30%)
GELUCIRE 44/14 (about 40%); Vitamin E TPGS (about 30%); MIGLYOL 812 (about 30%)
GELUCIRE 44/14 (about 40%); Vitamin E TPGS (about 20%); MIGLYOL 812 (about 40%)
GELUCIRE 44/14 (about 30%); Vitamin E TPGS (about 30%); MIGLYOL 812 (about 40%)
GELUCIRE 44/14 (about 20%); Vitamin E TPGS (about 30%); MIGLYOL 812 (about 50%)
Vitamin E TPGS (about 50%); MIGLYOL 812 (about 50%)
GELUCIRE. 44/14 (about 60%); Vitamin E TPGS (about 25%); MIGLYOL 812 (about 15%)
GELUCIRE 50/13 (about 30%); Vitamin E TPGS (about 5%); MIGLYOL 812 (about 65%)
GELUCIRE 50/13 (about 50%): MIGLYOL 812 (about 50%)
GELUCIRE 50/13 (about 50%); Vitamin E TPGS (about 10%); MIGLYOL 812 (about 40%)
GELUCIRE 50/13 (about 50%); Vitamin E TPGS (about 20%); MIGLYOL 812 (about 30%)
GELUCIRE 50/13 (about 40%); Vitamin E TPGS (about 30%); MIGLYOL 812 (about 30%)
GELUCIRE 50/13 (about 40%): Vitamin E TPGS (about 20%); MIGLYOL 812 (about 40%)
GELUCIRE 50/13 (about 30%); Vitamin E TPGS (about 30%); MIGLYOL 812 (about 40%)
GELUCIRE 50/13 (about 20%); Vitamin E TPGS (about 30%); MIGLYOL 812 (about 50%)
GELUCIRE 50/13 (about 60%); Vitamin E TPGS (about 25%); MIGLYOL 812 (about 15%)
GELUCIRE 44/14 (about 50% PEG 4000 (about 50%;
GELUCIRE 50/13 (about 50% PEG 4000 (about 50%;
Vitamin E TPGS (about 50%); PEG 4000 (about 50%)
GELUCIRE 44/14 (about 33.3%); Vitamin E TPGS (about 33.3%) PEG 4000 (about 33.3%)
GELUCIRE 50/13 (about 33.3%); Vitamin E TPGS (about 33.3%); PEG 4000 (about 33.3%)
GELUCIRE 44/14 (about 50%); Vitamin E TPGS (about 50%)
GELUCIRE 50/13 (about 50%); Vitamin E TPGS (about 50%)
Vitamin E TPGS (about 5%); MIGLYOL 812 (about 95%)
Vitamin E TPGS (about 5%); MIGLYOL 812 (about 65%); PEG 4000 (about 30%)
Vitamin E TPGS (about 10%); MIGLYOL 812 (about 90%)
Vitamin E TPGS (about 5%); MIGLYOL 812 (about 85%); PEG 4000 (about 10%)
Vitamin E TPGS (about 10%); MIGLYOL 812 (about 80%); PEG 4000 (about 10%).

In one embodiment of the invention, the pharmaceutical compositions comprise an active vitamin D compound, a lipophilic component, and a surfactant. The lipophilic component may be present in any percentage from about 1% to about 100%. The lipophilic component may be present at about 1, 2, 3, 4, 5, 6, 7, 8, 9, 10, 11, 12, 13, 14, 15, 16,-17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 61, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. The surfactant may be present in any percentage from about 1% to about 100%. The surfactant may be present at about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 61, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100%. In one embodiment, the lipophilic component is MIGLYOL 812 and the surfactant is vitamin E TPGS. In preferred embodiments, pharmaceutical compositions comprise about 50% MIGLYOL 812 and about 50% vitamin E TPGS; about 90% MIGLYOL 812 and about 10% vitamin E TPGS; or about 95% MIGLYOL 812 and about 5% vitamin E TPGS.

In another embodiment of the invention, the pharmaceutical compositions comprise an active vitamin D compound, and a lipophilic component, e.g., around 100% MIGLYOL 812.

In a preferred embodiment, the pharmaceutical compositions comprise about 50% MIGLYOL 812, about 50% vitamin E TPGS, and small amounts of BHA and BHT. This formulation has been shown to be unexpectedly stable, both chemically and physically (see, e.g., U.S. Patent Application Publication No. 2006/0189586). The enhanced stability provides the compositions with a longer shelf life. Importantly, the stability also allows the compositions to be stored at room temperature, thereby avoiding the complication and cost of storage under refrigeration. Additionally, this composition is suitable for oral administration and has been shown to be capable of solubilizing high doses of active vitamin D compound, thereby enabling high dose pulse administration of active vitamin D compounds for the treatment of hyperproliferative diseases and other disorders.

The pharmaceutical compositions comprising the active vitamin D compound of the present invention may further comprise one or more additives. Additives that are well known in the art include, e.g., detackifiers, anti-foaming agents, buffering agents, antioxidants (e.g., ascorbyl palmitate, butyl hydroxy anisole (BHA), butyl hydroxy toluene (BHT) and tocopherols, e.g., α-tocopherol (vitamin E)), preservatives, chelating agents, viscomodulators, tonicif[iota]ers, flavorants, colorants odorants, opacifiers, suspending agents, binders, fillers, plasticizers, lubricants, and mixtures thereof. The amounts of such additives can be readily determined by one skilled in the art, according to the particular properties desired. For example, antioxidants may be present in an amount of from about 0.05% to about 0.35% by weight based upon the total weight of the composition.

The additive may also comprise a thickening agent. Suitable thickening agents may be those known and employed in the art, including, e.g., pharmaceutically acceptable polymeric materials and inorganic thickening agents. Exemplary thickening agents for use in the present pharmaceutical compositions include polyacrylate and polyacrylate co-polymer resins, for example poly-acrylic acid and poly-acrylic acid/methacrylic acid resins; celluloses and cellulose derivatives including: alkyl celluloses, e.g., methyl-, ethyl- and propyl-celluloses; hydroxyalkyl-celluloses, e.g., hydroxypropyl-celluloses and hydroxypropylalkyl-celluloses such as hydroxypropyl-methyl-celluloses; acylated celluloses, e.g., cellulose-acetates, cellulose-acetatephthallates, cellulose-acetatesuccinates and hydroxypropylmethyl-cellulose phthallates; and salts thereof such as sodium-carboxymethyl-celluloses; polyvinylpyrrolidones, including for example poly-N-vinylpyrrolidones and vinylpyrrolidone co-polymers such as vinylpyrrolidone-vinylacetate co-polymers; polyvinyl resins, e.g., including polyvinylacetates and alcohols, as well as other polymeric materials including gum traganth, gum arabicum, alginates, e.g., alginic acid, and salts thereof, e.g., sodium alginates; and inorganic thickening agents such as atapulgite, bentonite and silicates including hydrophilic silicon dioxide products, e.g., alkylated (for example methylated) silica gels, in particular colloidal silicon dioxide products.

Such thickening agents as described above may be included, e.g., to provide a sustained release effect. However, where oral administration is intended, the use of thickening agents as aforesaid will generally not be required and is generally less preferred. Use of thickening agents is, on the other hand, indicated, e.g., where topical application is foreseen.

Compositions in accordance with the present invention may be employed for administration in any appropriate manner, e.g., orally, e.g., in unit dosage form, for example in a solution, in hard or soft encapsulated form including gelatin encapsulated form, parenterally or topically, e.g., for application to the skin, for example in the form of a cream, paste, lotion, gel, ointment, poultice, cataplasm, plaster, dermal patch or the like, as a coating for a medical device, e.g., a stent, or for ophthalmic application, for example in the form of an eye-drop, -lotion or -gel formulation. Readily flowable forms, for example solutions and emulsions, may also be employed e.g., for intralesional injection, or may be administered rectally, e.g., as an enema.

When the composition of the present invention is formulated in unit dosage form, the active vitamin D compound will preferably be present in an amount of between 1 and 1000 μg per unit dose. More preferably, the amount of active vitamin D compound per unit dose will be about 1, 2, 3, 4, 5, 6, 7, 8, 9, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 250, 300, 350, 400, 450, 500, 550, 600, 650, 700, 750, 800, 850, 900, 950 or 10000 μg or any amount therein. In a preferred embodiment, the amount of active vitamin D compound per unit dose will be about 5 μg to about 180 μg, more preferably about 10 μg to about 135 μg, more preferably about 45 μg. In one embodiment, the unit dosage form comprises 7, 15, 30, 35, 45, 90, 135, or 180 μg of calcitriol.

When the unit dosage form of the composition is a capsule, the total quantity of ingredients present in the capsule is preferably about 10-1000 μL. More preferably, the total quantity of ingredients present in the capsule is about 100-300 μL. In another embodiment, the total quantity of ingredients present in the capsule is preferably about 10-1500 mg, preferably about 100-1000 mg. In one embodiment, the total quantity is about 225, 450, 675, or 900 mg. In one embodiment, the unit dosage form is a capsule comprising 7, 15, 30, 35, 45, 90, 135, or 180 μg of calcitriol.

Subjects which may be treated according to the present invention include all animals which may benefit from administration of the compounds of the present invention. Such subjects include humans, pets such as dogs and cats, and veterinary animals such as cows, pigs, sheep, goats and the like.

The following examples are illustrative, but not limiting, of the methods of the present invention. Other suitable modifications and adaptations of the variety of conditions and parameters normally encountered in medical treatment and pharmaceutical science and which are obvious to those skilled in the art are within the spirit and scope of the invention.

EXAMPLES

Intestinal Fibrosis

A particularly relevant animal model for radiation toxicity is described in Wang et al., *J. Thromb. Haemost,* 2(11):2027-2035 (2004)). In brief, a "scrotal hernia" containing a 4 cm loop of distal ileum is surgically created in male Sprague-Dawley rats. After a 3 week recovery period, the scrotal hernia is irradiated locally without exposing the rest of the animal to ionizing radiation.

After creation of the scrotal hernias in rats, the rats are subjected to treatment with: vehicle control (i.e., 0.4% methyl cellulose) or with a formulation containing calcitriol. The calcitriol containing formulation could be administered at doses ranging from about 0.1 μg/kg/day to about 1 μg/kg/day of a formulation containing calcitriol. The treatments are administered every three days for about 10 days, starting the daily before irradiation (i.e., the drug may be administered on day-1, day 2, day 5, day 8). Beginning on day 1, the scrotal hernia of each animal is irradiated locally by exposure to 5 Gy for 9 days. After an additional 2 week observation period following treatment, the rats are euthanized and assessed for radiation toxicity using these endpoints: structural radiation injury, immunohistochemistry (e.g., neutrophil infiltration, collagen type III deposition, smooth muscle cell proliferation, extracellular matrix-associated TGF-β immunoreactivity, collagen type I deposition, macrophages (ED-2)), and morphometry.

Structural Radiation Injury

Structural radiation injury is assessed in hematoxylin-eosin-stained sections using a radiation injury score system previously described (see, Langberg et al., *Acta Oncol,* 31(7): 781-787 (1992); and Hauer-Jensen et al., *Acta Radiol Oncol,* 22(4):299-303 (1983)). In brief, seven parameters of radiation injury (mucosal ulcerations, epithelial atypia, thickening of subserosa, vascular sclerosis, intestinal wall fibrosis, ileitis cystica profunda, and lymph congestion) are graded (0-3) according to severity. The sum of the scores for the individual alterations constitutes the Radiation Injury Score. All specimens can be evaluated by two separate researchers and non-concordant scores can be resolved by consensus.

Immunohistochemistry

Quantitative immunohistochemistry is used to determine: (i) neutrophil infiltration by myeloperoxidase staining; (ii) intestinal smooth muscle cell proliferation using proliferation cell nuclear antigen (PCNA) labeling index; (iii) collagen deposition by staining for collagen types I and III; (iv) extracellular matrix-associated transforming growth factor (TGF)-$\beta$, and (v) macrophage ED-2. Immunohistochemical staining is performed with appropriate positive and negative controls using the avidin-biotin complex (ABC) technique previously described by Wang et al., *J. Thromb. Haemost*, 2(11):2027-2035 (2004). Primary antibodies, catalog numbers, incubation times, dilutions, and companies are, for example: polyclonal antimyeloperoxidase antibody (A0398, 2 h, 1:100; Dako, Carpinteria, Calif., USA); monoclonal anti-PCNA antibody (NA03, 2 h, 1:100; Calbiochem, Cambridge, Mass., USA); polyclonal antibodies against collagen type I (1310-01, 2 h, 1:100 dilution; Southern Biotechnology Associates, Birmingham, Al., USA); collagen type III (1330-01, 2 h, 1:100 dilution, Southern Biotechnology Associates); polyclonal rabbit anti-TGF-$\beta$ antibody (AB-100-NA, 2 h, 1:300 dilution; R&D, Minneapolis, Minn., USA); and ED-2 (MCA342, 2 h, 1:100 dilution, Serotec, Rahway, N.C., USA).

Computerized image analysis is performed as previously described (see, Wang et al., *Thromb. Haemost.*, 87(1):122-128(2002); Wang et al., *J. Pharmacol. Exp. Ther.*, 297(1):35-42 (2001)). Neutrophil infiltration was assayed by identifying myeloperoxidase-positive cells as previously described (see, Wang et al., *Thromb. Haemost*, 87(1):122-128(2002)). Areas positive for collagen types I and III deposition were measured as previously described (see, Raviv et al., *World J. Urol.*, 15(1):50-55 (1997); and Wang et al., *Thromb. Haemost*, 87(1):122-128 (2002)). Extracellular matrix-associated TGF-$\beta$ immunoreactivity was measured as previously described (see, Richter et al., *Radiother. Oncol.*, 39(3):243-251 (1996)).

Morphometry

The thickness of the intestinal wall proper (submucosa, muscularis externa, and subserosa, but excluding the mucosa) is measured with an eyepiece linear microruler. Five measurements, 500 µm apart, are obtained, averaged for each specimen, and used as a single value for statistical calculations.

The surface area of the intestinal mucosa is measured in vertical sections using a projection/cycloid method previously described (see Baddeley et al., *J. Microsc.*, 142(Pt 3):259-276 (1986); and Langberg et al., *Acta Oncol.*, 35(1): 81-87 (1996)). This technique does not require assumptions about the shape or orientation distribution of the specimens and thus circumvents problems associated with other similar procedures for surface area measurement.

Statistical Methods

Differences in endpoints as a function of drug treatment are assessed using fixed-factor analysis of variance and post hoc comparisons with Newman-Keul's test (NCSS2000 for Windows 95, NCSS, Kaysville, Utah., USA). Univariate comparisons were performed with the Mann-Whitney U-test using StatXact 5 (Cytel Software, Cambridge, Mass., USA), a software package for exact non-parametric inference.

Additional Endpoints

Immunohistochemistry

In addition to the quantitative immunohistochemical analysis mentioned above, quantitative immunohistochemical analysis of TM may be performed as previously described (see, Wang et al., *Am. J. Pathol*, 160(6):2063-2072 (2002).

Morphometry

In addition to the morphometric analysis mentioned above, morphometric analysis of radiation-induced vascular sclerosis may be performed using computer-assisted image analysis as described previously (see, Langberg et al., *Acta Oncol.*, 35(1):81-87 (1996)). In brief, the total and luminal cross-sectional areas of submucosal vessels in the range 10-130 µm (the range of most affected by radiation) are measured (10 vessels per slide). Vessel wall ratio is calculated as the ratio between the total cross-sectional area and the vessel wall area (total cross-sectional area minus luminal cross-sectional area). The relationship between vessel wall area and total cross-sectional area is linear, and the average vessel wall ratio in each specimen is thus used as a single value for statistical purposes.

Dye Elution Method for Collagen Determination

Collagen content is determined using the dye elution method of Lopez-de Leon (Lopez-de Leon and Rojkind, *J. Histochem. Cytochem.*, 33:737-747 (1985)) adapted to our model system (Langberg et al., *Acta Oncol.*, 35:81-87 (1996)). In heterogeneous organs like intestine, the dye elution method produces more consistent data and is less influenced by changes in structures other than connective tissue compared to the more commonly used hydroxyproline assay (Hauer-Jensen et al., *Acta Radiol Oncol.*, 25:137-142 (1986)). An additional advantage is that the method also provides direct morphologic correlates to the measured collagen content.

The present invention is not to be limited in scope by the specific embodiments described herein. Indeed, various modifications of the invention in addition to those described herein will become apparent to those skilled in the art from the foregoing description. Such modifications are intended to fall within the scope of the appended claims.

Various publications are cited herein, the disclosures of which are incorporated by reference in their entireties.

What is claimed:

1. A method for treating oral mucositis in a subject in need thereof comprising administering to the subject a therapeutically effective amount of an active vitamin D compound.

2. The method of claim 1, wherein the active vitamin D compound is selected from the group consisting of calcitriol, 1α-cacidol and calcifediol.

3. The method of claim 1, wherein the active vitamin D compound is calcitriol.

4. The method of claim 1, wherein the active vitamin D compound is administered by high pulse dose administration.

5. The method of claim 4, wherein the high dose pulse administration is administered no more frequently than once in three days.

6. The method of claim 1, wherein the active vitamin D compound is administered in an amount sufficient to reach supraphysiologic levels without inducing severe symptomatic hypercalcemia.

7. The method of claim 1, wherein the active vitamin D compound is administered in an amount sufficient to reach blood plasma levels greater than about 0.25 nM.

8. The method of claim 1, wherein the active vitamin D compound is administered in an amount sufficient to reach blood plasma levels equal to or greater than 1 nM.

9. The method of claim 1, wherein the active vitamin D compound is administered in an amount sufficient to reach blood plasma levels equal to or greater than 1 nM within 2 to 36 hours after administration.

10. The method of claim 1, wherein the active vitamin D compound is administered in an amount sufficient to maintain the subject's plasma level of the active vitamin D compound at or above 1 nM for 24 hours.

11. The method of claim 1, wherein the active vitamin D compound is administered in an amount sufficient to achieve an area under the curve concentration of equal to or greater than 24 nM·hour.

12. The method of claim 1, wherein the active vitamin D compound is administered at a dose of about 15 μg to about 1 mg.

13. The method of claim 1, wherein the active vitamin D compound is administered at a dose of about 15 μg to 60 μg.

14. The method of claim 1, wherein the active vitamin D compound is administered at a dose of about 30 μg to 60 μg.

15. The method of claim 1, wherein the active vitamin D compound is administered at a dose of about 45 μg.

16. The method of claim 1, wherein the subject in need thereof is a cancer patient.

17. The method of claim 16, wherein the subject in need thereof does not have androgen induced prostate cancer.

18. The method of claim 1, wherein the mucositis is caused by radiation-induced toxicity in non-malignant tissue.

19. The method of claim 1, wherein the mucositis is caused by chemical-induced toxicity in non-malignant tissue.

20. The method of claim 19, wherein the chemical-induced toxicity is not caused by docetaxel.

21. The method of claim 1, wherein the active vitamin D compound is administered as a unit dosage form comprising about 10 μg to about 75 μg of calcitriol, about 50% MIGLYOL 812 and about 50% tocopherol peg-1000 succinate.

22. The method of claim 21, wherein the active vitamin D compound is administered as a unit dosage form comprising about 45 μg of calcitriol, about 50% MIGLYOL 812 and about 50% tocopherol peg-1000 tocopherol.

23. The method of claim 21, wherein the active vitamin D compound is administered as a unit dosage form comprising about 15 μg of calcitriol, about 50% MIGLYOL 812 and about 50% tocopherol peg-1000 tocopherol.

24. The method of claim 22 wherein the unit dosage form further comprises butylated hydroxyanisole and butylated hydroxytoluene.

25. The method of claim 23 wherein the unit dosage form further comprises butylated hydroxyanisole and butylated hydroxytoluene.

26. The method of claim 1, wherein the active vitamin D compound is administered orally, intravenously, parenterally, rectally, sublingually, intramuscularly, topically, nasally or transdermally.

27. The method of claim 26, wherein the active vitamin D compound is administered orally.

28. The method of claim 26, wherein the active vitamin D compound is administered intravenously.

29. The method of claim 1, wherein the active vitamin D compound is administered in combination with radiation therapy.

30. The method of claim 1, wherein the active vitamin D compound is administered in combination with chemotherapy.

31. The method of claim 1, wherein the active vitamin D compound is administered in combination with one or more therapeutic agents.

32. The method of claim 31, wherein the active vitamin D compound is administered in combination with a protease activated receptor-1 inhibitor.

33. The method of claim 31, wherein the active vitamin D compound is administered in combination with an agent selected from the group consisting of: a PAR-1 inhibitor, palifermin, glutamine, L-glutamine, teduglutide, sucralfate mouth rinses, iseganan, lactoferrin, mesna, trefoil factor, and CASAD; or a combination of two or more of the above.

* * * * *